(12) United States Patent
Mancini

(10) Patent No.: US 8,481,481 B2
(45) Date of Patent: Jul. 9, 2013

(54) PEPTIDES AND THEIR USE AS CARRIERS INTO CANCER CELLS

(75) Inventor: Aldo Mancini, Naples (IT)

(73) Assignee: Advanced Accelerator Applications S.A., Saint Genis Pouilly (FR)

( * ) Notice: Subject to any disclaimer, the term of this patent is extended or adjusted under 35 U.S.C. 154(b) by 128 days.

(21) Appl. No.: 13/003,568

(22) PCT Filed: Jul. 8, 2009

(86) PCT No.: PCT/IB2009/052966
§ 371 (c)(1),
(2), (4) Date: Jan. 10, 2011

(87) PCT Pub. No.: WO2010/004513
PCT Pub. Date: Jan. 14, 2010

(65) Prior Publication Data
US 2011/0111043 A1 May 12, 2011

(30) Foreign Application Priority Data
Jul. 8, 2008 (IT) .................................. FI2008A0124

(51) Int. Cl.
*A61K 38/08* (2006.01)
*A61K 38/12* (2006.01)

(52) U.S. Cl.
USPC .......... 514/1.2; 514/19.2; 514/21.1; 514/21.7

(58) Field of Classification Search
None
See application file for complete search history.

(56) References Cited

U.S. PATENT DOCUMENTS
7,470,661 B2 * 12/2008 Shone et al. ................... 514/1.1

FOREIGN PATENT DOCUMENTS
WO 00/28041 5/2000
WO 2004/083231 9/2004
WO 2006/095837 9/2006

OTHER PUBLICATIONS

St. Clair et al. "Complementary DNA Encoding Human Colon Cancer Manganese Superoxide Dismutase and the Expression of Its Gene in Human Cells," Cancer Research 51, 939-943, Feb. 1, 1991.*
PCT International Search Report for PCT/IB2009/052966 filed Jul. 8, 2009 in the name of Advanced Accelerator Applications S.A.
PCT International Preliminary Report on Patentability for PCT/IB2009/052966 filed Jul. 8, 2009 in the name of Advanced Accelerator Applications S.A.
PCT Written Opinion for PCT/IB2009/052966 filed Jul. 8, 2009 in the name of Advanced Accelerator Applications S.A.
Borrelli A et al, "Chimeric manganese-super oxide dismutase-2 (Mn-SOD-2) secreted from a human liposarcoma with specific and selective cytoxic activity on tumor cells expressing estrogen receptors (RE)", Molecular & Cellular Proteomics 2004, 3: S195.
Mancini A et al, "Tumor suppressive activity of a variant isoform of manganese superoxide dismutase released by a human liposarcoma cell line", International Journal of Cancer 2006, 119: 932-943.
Pedram Ali et al, "Functional estrogen receptors in the mitochondria of breast cancer cells", Molecular Biology of the Cell 2006, 17: 2125-2137.
Borrelli A et al, "A recombinant MnSOD is radioprotective for normal cells and radiosensitizing for tumor cells.", Free Radical Biology & Medicine 2009, 46: 110-116.
Mancini A et al, "Biophysical and biochemical characterization of a liposarcoma-derived recombinant MnSOD protein acting as an anticancer agent", International Journal of Cancer 2008, 123: 2684-2695.

* cited by examiner

*Primary Examiner* — Christina Bradley
(74) *Attorney, Agent, or Firm* — Steinfl & Bruno LLP

(57) ABSTRACT

The use of a peptide is described as a carrier for the transport of molecules or radioisotopes into cancer cells; also described are modifications of said peptide and their use.

16 Claims, 2 Drawing Sheets

SEQUENCE LISTING

<160> NUMBER OF SEQ ID NOS: 4

<210> SEQ ID NO 1
<211> LENGTH: 24
<212> TYPE: PRT
<213> ORGANISM: Artificial sequence
<220> FEATURE:
<223> OTHER INFORMATION: peptide made by synthesis

```
<220> FEATURE:
<221> NAME/KEY: peptide
<222> LOCATION: (1)..(24)
<223> OTHER INFORMATION: leader peptide of rMnSOD and of LSA-type-MnSOD

<400> SEQUENCE: 1

Met Leu Ser Arg Ala Val Cys Gly Thr Ser Arg Gln Leu Ala Pro Ala
1               5                   10                  15

Leu Gly Tyr Leu Gly Ser Arg Gln
            20

<210> SEQ ID NO 2
<211> LENGTH: 7
<212> TYPE: PRT
<213> ORGANISM: Artificial sequence
<220> FEATURE:
<223> OTHER INFORMATION: peptide made by synthesis

<400> SEQUENCE: 2

Met Leu Ser Arg Ala Val Cys
1               5

<210> SEQ ID NO 3
<211> LENGTH: 8
<212> TYPE: PRT
<213> ORGANISM: Artificial sequence
<220> FEATURE:
<223> OTHER INFORMATION: peptide made by synthesis
<220> FEATURE:
<221> NAME/KEY: peptide
<222> LOCATION: (1)..(8)
<223> OTHER INFORMATION: Cyclic peptide: Cys1 and Cys8 are bonded by a
      disulphide bond.

<400> SEQUENCE: 3

Cys Met Leu Ser Arg Ala Val Cys
1               5

<210> SEQ ID NO 4
<211> LENGTH: 7
<212> TYPE: PRT
<213> ORGANISM: Artificial sequence
<220> FEATURE:
<223> OTHER INFORMATION: peptide made by synthesis
<220> FEATURE:
<221> NAME/KEY: peptide
<222> LOCATION: (1)..(7)
<223> OTHER INFORMATION: Cyclic peptide: Cys1 and Cys7 are bonded by a
      disuplhide bond

<400> SEQUENCE: 4

Cys Leu Ser Arg Ala Val Cys
1               5
```

PEPTIDES AND THEIR USE AS CARRIERS INTO CANCER CELLS

CROSS REFERENCE TO RELATED APPLICATIONS

The present application is the US national stage of International Application PCT/IB2009/052966 filed on Jul. 8, 2009 which, in turn, claims priority to Italian Patent Application FI2008A000124 filed on Jul. 8, 2008.

FIELD OF THE INVENTION

The invention relates to the field of products usable for diagnostic or therapeutic purposes in the analysis or treatment of cancer cells.

STATE OF THE ART

The relevance of chromosomal anomalies in the development of tumours has been known since the last century However it is only within the last twenty years, with the development of cytogenetics and molecular biology, that the principles of neoplasia genetics have been definitely confirmed and chromosomal alterations have been recognized as critical for tumour pathogenesis in man.

In a recent study a liposarcoma cell line was examined and found to produce and secrete various proteins in its culture medium. Among these, in particular, a manganese superoxide dismutase (known as LSA-type-MnSOD) was identified which, in addition to enzyme activity aimed at transforming free radicals into hydrogen peroxide (common to all SOD), demonstrated structural and functional properties such as to differentiate it from the corresponding MnSOD expressed by the myeloid leukemia cell line U937.

In this respect LSA-Type-MnSOD is secreted by LSA cells whereas native MnSOD is localized in the mitochondrial matrix, the former having a significantly higher molecular weight (30 kDa) than native MnSOD (24 kDa).

Moreover if LSA-type-MnSOD is injected in vivo or in vitro, it is able to reach all cells and, on reacting with the free radicals present therein, produces hydrogen peroxide. The toxicity threshold is however attained more easily in tumour cells than normal cells because tumour cells, not having sufficient amounts of catalase, are unable to metabolize this peroxide. This results in the preferential inhibition of proliferation and an increase in tumour cell deaths only. This aspect confirms that LSA-type-MnSOD is cytotoxic specifically and selectively to tumour cells.

A recombinant form of LSA-type-MnSOD (rMnSOD) produced by specific cDNA clones has also been shown to retain the structural and oncotoxic properties of the native protein, moreover both extractive LSA-type-MnSOD and rMnSOD bear a 24-residue peptide at the N-terminus which corresponds precisely to the leader sequence of MnSOD.

DETAILED DESCRIPTION OF THE INVENTION

Figure 1:
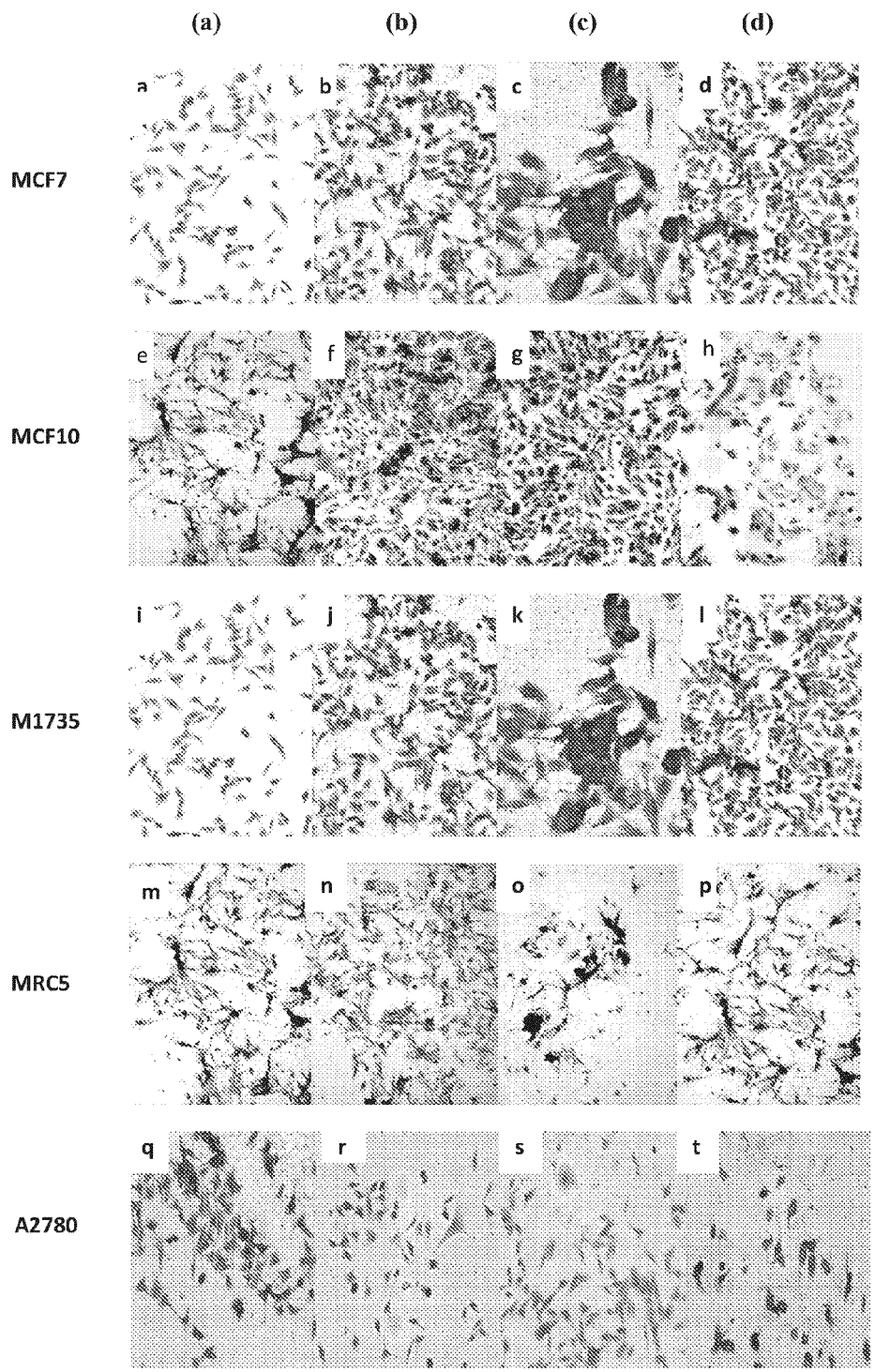
FIG. 1 (a-d) shows the action on various cell lines of cisplatin alone (d), of cisplatin conjugated to the leader peptide of rMnSOD (c) and of the leader peptide of rMnSOD alone (b) compared to the negative control (a).

It has now been surprisingly found that the peptide of sequence:

MLSRAVCGTSRQLAPALGYLGSRQ        (SEQ 1)

which represents the leader peptide of rMnSOD and, in view of its similarity to the above, also that of LSA-type-MnSOD, is able to penetrate cancer cells and can therefore act as a carrier for transporting into said cells molecules or radioisotopes usable for therapeutic or diagnostic purposes.

According to a further embodiment, the invention also relates to a peptide of the following sequence:

MLSRAVC        (SEQ 2)

which is also able to act as a carrier in a similar manner to the above peptide (SEQ. 1)

Furthermore the invention also relates to a peptide obtained either by inserting a cysteine into the previously described heptapeptide (bound to the N-terminus methionine) or by substituting said methionine with a cysteine and cyclizing to form a disulphide bridge between said inserted cysteine and the cysteine already present; said peptides have therefore the following respective sequences:

CMLSRAVC        (SEQ 3)

CLSRAVC         (SEQ 4)

in which the two terminal cysteines are linked together by a disulphide bridge.

The invention also relates to conjugates of the leader peptide as aforedescribed with chelating groups able to bind radioisotopes (such as DOTA, DTPA, NOTA, HYNIC, etc.), dyes such as fluorescein, rhodamine, etc. i.e. molecules having cytostatic properties such as cisplatin, taxol, pharmorubicin etc., or molecules having enzyme activity such as kinase inhibitors able to prevent mitotic signal transduction, and also antisense oligonucleotides (o.n.).

Additionally, if required, the leader peptide (SEQ 1) already conjugated to cisplatin (a complex hereinafter referred to as rMnSOD-Lp-CC) can be further conjugated to biopolymers or with liposomes and used to conduct antitumour therapies by means of oral or subcutaneous administration.

The invention therefore also relates to a formulation for the controlled release of rMnSOD-Lp-CC. Said formulations can for example include microspheres in biodegradable materials such as: hyaluronic acid, PEG, poly(lactic-co-glycolic) acid (PLGA) and other biodegradable and biocompatible copolymers of well-established use in the pharmaceutical sector.

If PLGA is used, PLGAs having different lactic-glycolic ratios (75:25 and 50:50), and different molecular weights and varying hydrophilicities can be utilized, with the aim of evaluating how the polymer properties influence microsphere characteristics; for example Resomer® RG 504 H and Resomer® RG 756 (or their equivalents), having respective intrinsic viscosities of 0.5 and 0.8 dl/g and molecular weights (Mw) of 20,000 and 89,000 Da, could be used.

In a similar manner to that described above, the leader peptide conjugated to DOTA and bound to biopolymers or liposomes can also be used as a molecular carrier for nanotechnological processes, the methods of which have already been approved by the US FDA.

Moreover, rMnSOD-Lp-CC can be used to carry out predictive tests (by immunocytochemical techniques) in order to understand whether antitumor therapy using rMnSOD-Lp-CC could have an effect on tumours.

In this respect, if histological cryostat sections of tumours are treated with rMnSOD-Lp-CC for 60 minutes and, after fixing with Zamboni liquid, are treated with antibodies against rMnSOD, it could be ascertained whether the tumour tissue cells have incorporated the rMnSOD-Lp-CC.

A positive results means that if rMnSOD-Lp-CC is injected into that tumour-affected organism, it will reach the tumour and destroy it.

Furthermore, by comparing the capacity of rMnSOD-Lp-CC to penetrate tumour cells and the presence of oestrogen receptors of these cells it will be possible, by means of the immunocytochemical analysis described, to demonstrate the degree of oestrogen receptor expression of that tumour.

The invention therefore relates to pharmaceutical compositions for the treatment of tumour diseases and to diagnostic methods comprising at least one conjugate as aforedescribed.

The invention will be better understood in the light of the following examples.

EXAMPLE 1

Synthesis of the Peptide of Sequence
MLSRAVCGTSRQLAPALGYLGSRQ (SEQ 1)

The 24-amino acid peptide leader (SEQ 1) was synthesized using solid phase synthesis techniques with standard Fmoc methodology in a manual reactor. Purification was carried out with semi-preparative RP-HPLC using a C18-bonded silica column (Vydac 218TP1010). The peptide was 99% pure; the molecular mass of the peptide was confirmed by mass spectrometry and amino acid analysis.

EXAMPLE 2

Conjugation of the Peptide of Sequence
MLSRAVCGTSRQLAPALGYLGSRQ (SEQ 1)
with DOTA and Labelling of the Complex with
$^{68}$Ga.

The synthetic leader peptide obtained in example 1 was then conjugated to 20 μg of DOTA and with radioactive $^{68}$Ga at 120° C. for 15 minutes in Hepes buffer. The labelled peptide was than purified by reverse phase chromatography on a small C18 column, washed with water and dried by air flow.

The peptide was then re-dissolved in 400 μl of 96% ethanol.

The same peptide was labelled with $^{90}$Y, $^{177}$Lu, $^{111}$In at 90° for 30 minutes in acetic acid/sodium acetate buffer or in gentisic buffer.

Analyses were carried out on the leader peptide of the rMnSOD conjugated to DOTA to determine its stability in physiological solution. The peptide was found to be stable for 48 hours without showing any change in its physico-chemical structure.

EXAMPLE 3

Conjugation of the Peptide of Sequence
MLSRAVCGTSRQLAPALGYLGSRQ (SEQ 1)
with Fluorescein Labelling at the N-terminus of the parent peptide MLSRAVCGTRQLAPALGYLLGSRQ and its shorter analogue MLSRAVC was carried out in solid phase by means of a standard coupling protocol using 5(6)-carboxyfluorescein (FAM).

EXAMPLE 4

Synthesis of the Peptide of Sequence MLSRAVC
(SEQ 2)

The peptide formed from the first 7 amino acids of the peptide sequence obtained in example 1 was synthesized using solid phase synthesis techniques with standard Fmoc methodology in a manual reactor. Purification was carried out by semi-preparative RP-HPLC using a C-18 bonded silica column (Vydac 218TP1010). The peptide was 99% pure; molecular mass of the peptide was confirmed by mass spectrometry and amino acid analysis.

EXAMPLE 5

Cyclization of the Peptide SEQ 2

Two cyclic analogues were obtained from the peptide sequence MLSRAVC by introducing a second cysteine residue:

```
Analogue 1 CMLSRAVC        (SEQ 3)

Analogue 2 CLSRAVC         (SEQ 4)
```

Analogue 1: is derived from bonding with a cysteine added to the original peptide sequence at the methionine.

Analogue 2: is derived from substituting the N-terminus methionine of the original peptide with a cysteine residue.

The disulphide bridges were formed by the bond between the 2 SHs of the terminal cysteines.

Cyclization was achieved by adding a 0.1 M solution of $NH_4HCO_3$ in water to the peptide chain (10 ml of solution per 10 mg of peptide) followed by simple air oxidation at ambient temperature for about 48 hours.

The two derived cyclic peptides were bound to the chelating agent and labelled with $^{90}$Y, $^{177}$Lu, $^{111}$In at 90° C. for 30 minutes in acetic acid/sodium acetate buffer or in gentisic buffer.

EXAMPLE 6

1 mCi of the labelled conjugate obtained in example 2 was injected into a 13 year old female dog affected by multiple mammary tumours.

Scanning was undertaken about 30 minutes after the injection by a ECAT 47 PET scanner (Siemens) and the images were constructed in accordance with transaxial, coronal and sagittal planes.

EXAMPLE 7

MCF-7 cells were treated separately for 1 hour at ambient temperature with the conjugate obtained in example 3 and with a "scrambled" peptide, also labelled and used as the control, having the same amino acid composition but in a different sequence.

After treatment, the cells were examined using a confocal microscope.

A marked cytoplasmic fluorescence was visible in the cells incubated with the conjugate of example 3, whereas no fluorescence was seen in the controls treated with the scrambled peptide; this demonstrates that the labelled peptide was able to enter into the cells whereas the scrambled peptide did not show said capacity to penetrate cells.

EXAMPLE 8

Synthesis of the Complex Leader Peptide of rMnSOD Conjugated to Cisplatin

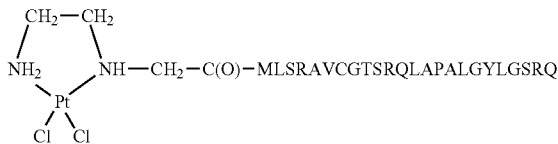

The leader peptide of rMnSOD, composed of 24 amino acids and having the sequence: MLSRAVCGTSRQLAPAL-GYLGSRQ, was synthesized by the solid phase Fmoc method in suitable reaction tubes.

The samples obtained were then purified by semi-preparative HPLC using a C18-bonded silica column (Vydac218TP1010).

The peptide was 99% pure, as confirmed by RP-HPLC analysis.

A diamino-ethyl-glycine was then bound to the peptide residue at the N-terminus position (M) which, by virtue of the presence of two free amino functions at a suitable distance (4 covalent bonds), is able to complex the Platinum(II) ions in the form of $PTCl_2$. The correct molecular weight and peptide mass were examined and confirmed by mass spectrometry analysis and amino acid sequence analysis, in accordance with the method of Stewart J M, Young J D. (Solid phase peptide synthesis).

EXAMPLE 9

Immunocytochemistry

The target cells (MCF-7) in continuous culture, derived from a mammary tumour of human origin, were incubated for three hours in the presence or absence of: (a) 24-amino acid leader peptide of rMnSOD-Lp-CC not conjugated to any other molecules, (b) 24-amino acid leader peptide conjugated to cisplatin.

After incubation, the cells were fixed with Zamboni fixative (solution composed of 4% paraformaldehyde+15% picric acid) for 60 minutes and washed with PBS. The cells were then maintained in PBS containing 0.3% hydrogen peroxide, with the aim of blocking endogenous peroxidases. The polyclonal antibody (anti-leader peptide of rMnSOD obtained from rabbit), diluted 1/200 was then added to the cells and left for 1 hour at ambient temperature. To develop the reaction, a DAKO SLAB Peroxidase K0679 kit was used.

EXAMPLE 10

Quantitative Determination Using Atomic Absorbance Spectrophotometry of Cisplatin Transported into Tumour Cells by the rMnSOD-leader Peptide The target cells MCF-7 were trypsinized, washed twice with buffered solution (PBS) and treated with 50 μl of 35% $HNO_3$ for 16 hours. The platin content was determined by subjecting the samples to atomic absorption with an Analyst 800 instrument, by Perkin-Elmer, Norwalk, Conn., USA, using the following parameters: pre-treatment temperature, 1300° C.; atomization temperature, 2200° C.; using as the matrix modifier a composition of 0.015 mg of Pt with 0.01 mg of $Mg(NO_3)_2$. The measurements were performed using the "Zeeman-effect background" correction system with Pyrolytic graphite-coated THGA tube (Perkin Elmer) and an integrated Lvov-type platform was used for metal determination. As standard solution we used a 2.5% $HNO_3$ solution (Spectrascan) to obtain three reference points on the calibration curve.

FIG. 1 shows from left to right the results obtained by treating cells of various normal cell lines (MCF10) and tumour cell lines (MCF7, M1735, MRC5 and A2780) with the leader peptide of rMnSOD (b), cells treated with the leader peptide conjugated to cisplatin (c) and finally, cells treated with cisplatin alone (d) and comparing to the respective untreated control cells (a). The immunohistochemical reaction demonstrated that the peptide on its own penetrated tumour cells without damaging the cells, whereas the peptide conjugated to cisplatin produced a strong apoptotic reaction after only three hours of incubation.

As can be seen from Table 1 below, the leader peptide of rMnSOD is able to transport into cells a quantity of cisplatin double the amount which enters cells if cisplatin alone is added to the tumour cells.

TABLE 1

| Quantity of cisplatin transported by the leader peptide of rMnSOD into tumour cells (quantification by atomic absorption) | | |
|---|---|---|
| MCF-7 Solution | Cisplatin 8.7 μg/l (3.5 μg Pt) | Pep-CisPT 9.4 μg/l (3.8 μg Pt) |
| MCF-7 Pellet. | 2.3 ng-Pt | 4.6 ng Pt |

Figure 2:
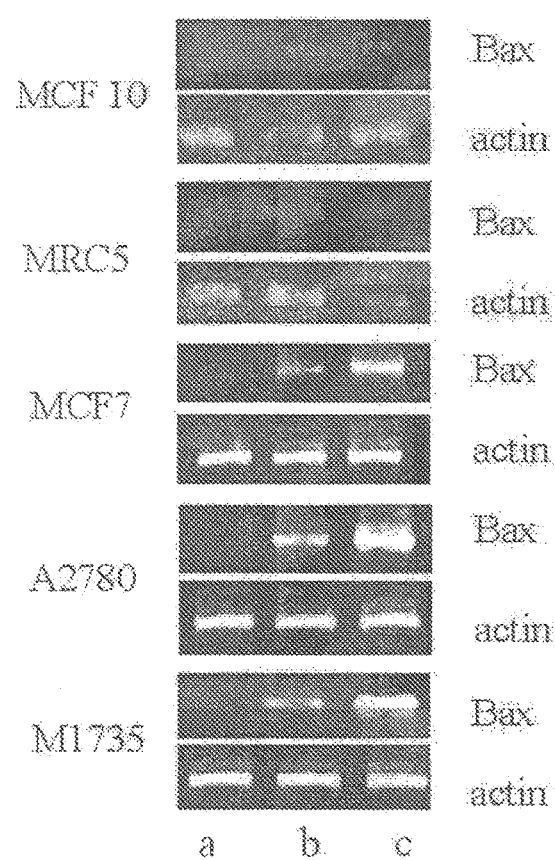
FIG. 2 shows that the apoptosis Bax gene is active only in tumour cells that have been treated in the presence of rMnSOD-Lp-CC.

FIG. 2 confirms the apoptotic action of the rMnSOD-Lp-CC complex on various cell lines.

As can be seen, treatment of all the normal cells in the presence of rMnSOD-Lp-CC does not induce any toxic reaction, demonstrated by the lack of Bax gene expression, this being the expression of an apoptotic reaction. This is in contrast to that which takes place in tumour cells, treated in the presence of rMnSOD-Lp-CC where the same gene is strongly expressed. In the experiment, actin cDNA was inserted as control of quantitative DNA expression; to note that again in this case (a) indicates untreated cells, (b) indicates cells treated with the leader peptide of rMnSOD (b), and (c) indicates cells treated with the leader peptide conjugated to cisplatin.

The invention claimed is:

1. A peptide consisting of the amino acid sequence CMLSRAVC (SEQ ID NO: 3) or CLSRAVC (SEQ ID NO: 4), wherein the terminal cysteines are linked together by a disulphide bridge.

2. A conjugate comprising a peptide and a dye, a molecule having cytostatic properties, a molecule having enzyme activity, an antisense oligonucleotide and/or a molecule with a chelating group able to bind to a radioisotope, wherein the peptide comprises the amino acid sequence CMLSRAVC (SEQ ID NO: 3) or CLSRAVC (SEQ ID NO: 4) or the peptide consists of the amino acid sequence MLSRAVC (SEQ ID NO: 2).

3. The conjugate of claim 2, wherein the molecule with a chelating group is DOTA, DTPA, NOTA, or HYNIC.

4. The conjugate of claim 2, wherein the dye is fluorescein or rhodamine.

5. The conjugate of claim 2, wherein the molecule having cytostatic properties is cisplatin, taxol, or pharmorubicin.

6. The conjugate of claim 2, wherein the molecule having cytostatic properties is cisplatin.

7. The conjugate of claim 2, wherein the molecule having enzyme activity is a kinase inhibitor able to prevent transduction of the mitotic signal.

8. A diagnostic agent comprising the conjugate of claim 2.

9. A pharmaceutical composition for treatment of a tumour disease, the pharmaceutical composition comprising the conjugate of claim 2.

10. A conjugate comprising a peptide and cisplatin, wherein the peptide comprises SEQ ID NO: 3 or SEQ ID NO: 4 or the peptide consists of SEQ ID NO: 2.

11. The conjugate of claim 10, wherein the conjugate is bound to DOTA, a biopolymer or a liposome.

12. A formulation for controlled release of the conjugate of claim 10, the formulation comprising a microsphere of a biodegradable material, the microsphere loaded with the conjugate.

13. The formulation of claim 12 wherein the biodegradable material is chosen from hyaluronic acid, PEG, poly(lactic-co-glycolic) acid (PLGA) and other biodegradable and biocompatible copolymers.

14. A molecular carrier for a nanotechnological process, the molecular carrier comprising the conjugate of claim 10.

15. A method to predict efficacy of an antitumor therapy, the method comprising contacting the conjugate of claim 10 with a tumour cell and detecting the incorporation of the conjugate of claim 10 in the tumour cell wherein detection of incorporation of the conjugate in the tumour cell is associated with predicted efficacy of the antitumor therapy.

16. A method for determining expression of an estrogen receptor of a tumour, the method comprising contacting the conjugate of claim 10 with the tumour; detecting the incorporation of the conjugate of claim 10 in the tumour; detecting the presence of estrogen receptor in the tumour; and comparing the detected conjugate incorporated in the tumour and the detected estrogen present in the tumour to determine the degree of expression of the estrogen receptor of the tumour.

* * * * *